United States Patent [19]

Doroshuk

[11] Patent Number: 4,620,550
[45] Date of Patent: Nov. 4, 1986

[54] IMPLANTABLE BIPOLAR STIMULATING ELECTRODE

[75] Inventor: Charles M. Doroshuk, Livingston, N.J.

[73] Assignee: Schering A.G., Berlin, Fed. Rep. of Germany

[21] Appl. No.: 723,389

[22] Filed: Apr. 15, 1985

[51] Int. Cl.⁴ ............................................. A61N 1/18
[52] U.S. Cl. .............................. 128/785; 128/419 P; 128/642
[58] Field of Search .................... 128/419 P, 639, 642, 128/783–789, 798

[56] References Cited

U.S. PATENT DOCUMENTS

| | | | |
|---|---|---|---|
| 2,536,271 | 1/1951 | Fransen | 128/798 |
| 3,244,174 | 4/1966 | Wesbey et al. | 128/419 P |
| 3,333,045 | 7/1967 | Fisher et al. | 128/784 |
| 3,543,761 | 12/1970 | Bradley | 128/784 |
| 4,144,889 | 3/1979 | Tyers et al. | 128/419 P |
| 4,155,353 | 5/1979 | Rea et al. | 128/642 |
| 4,407,303 | 10/1983 | Akerstrom | 128/419 P |
| 4,424,818 | 1/1984 | Doring et al. | 128/784 |

*Primary Examiner*—William E. Kamm
*Assistant Examiner*—Mitchell J. Shein
*Attorney, Agent, or Firm*—Elizabeth A. Bellamy; John R. Moses; I. William Millen

[57] ABSTRACT

A bipolar electrode is a disc of bio-compatable material. Wires are passed through the disc and terminate on one side in bead shaped electrode means of conductive material and out the other end to a power supply. The conductive material is, in one aspect, silver. In one embodiment, the disc is silicone rubber. In another and preferred embodiment the disc is of polypropylene mesh permitting tissue ingrowth and secure attachment.

8 Claims, 4 Drawing Figures

IMPLANTABLE BIPOLAR STIMULATING ELECTRODE

BACKGROUND OF THE INVENTION

This invention relates to a bio-compatible, implantable stimulating electrode, of the bipolar type, for chronic use, on atrial or ventricular surfaces of the heart, in experimental studies. In another aspect, the invention relates to such an electrode for use in conscious animal studies.

More particularly, the invention relates to an electrode for use in an animal testing PES program (Programmed Electrical Stimulation Testing), for testing of antiarrhythmic drugs. The type of testing which is conducted with the device of the present invention closely correlates to the PES testing done on humans to ascertain which antiarrhythmic drug is useful for their particular condition.

In the human case, a patient who has had a myocardial infarct is at risk of having another. Such a patient is then usually directed to a catheterization lab where he is catheterized to the heart. Ventricular tachycardia or fibrillation is induced and then converted to normal rhythm, and the patient is then tested with drugs to ascertain which antiarrhythmic drug decreases or prevents the fibrillation from occurring. The device of the present invention is for use in carrying over this type of testing to animals to avoid having to conduct it on humans while still reliably determining which antiarrhythmic drugs will work on humans.

In the prior art a number of electrodes have been developed to permit this type of PES testing. However, all suffer the disadvantage that they either cause extensive heart tissue damage with use, or have proven unreliable. More particularly, such devices include bipolar plunge wires, acrylic plaques and vinyl plaques. These items either work their way free from securing sutures because they do not flex with the animal heart, or the wires break where they joined the electrode.

Since considerable time and effort is involved in the preparation and study of these animals, it is vital that the electrodes used be reliable in performance over long periods of time and not cause extensive damage to the heart tissue. Many of the studies are conducted weeks or months after the initial surgical installation of the stimulating electrodes and because of the dog's impaired condition (myocardial infarct), it would not be feasible to re-instrument the dog if the electrode needed replacement because of malfunction.

A specific prior art implantable electrode structure, U.S. Pat. No. 4,125,116, is constructed so that the stimulating electrode conducting portion is embedded in a foam silicon rubber cushioning material so that the electrode structure will adapt more readily to the irregularities in the tissue surface. This structure, while attempting to provide for a secure attachment due to its flexibility, still encounters problems in use as discussed above since it will tend to separate from the tissue.

Another prior art electrode is disclosed in U.S. Pat. No. 4,030,509. This patent teaches a defibrillating electrode made of a metallic mesh which is insulated at its exterior surface by a layer of silicone rubber insulation. The electrode wraps around the heart in a complicated arrangement. This device includes a number of disadvantages since it cannot be readily adapted for experimental animal studies. Moreover, the relatively large metallic mesh, when in use, will often cause significant scarring and ultimate destruction of the tissue with which it is in contact.

U.S. Pat. No. 4,355,642, teaches a bipolar electrode manufactured of a mesh of synthetic fibers affixed to a disc. The mesh serves the purpose of permitting tissue ingrowth in the main electrode body to enhance attachment. A central spike or helix is required to penetrate the tissue to insure complete attachment. The spike or helix penetration causes damage within and without the surrounding tissue of the heart. The spike and helix are manufactured from platinum-iridium wire; another like structure is taught in U.S. Pat. No. 4,010,758.

SUMMARY OF THE INVENTION

It is thus an object of the present invention to provide a bipolar, bio-compatible implantable stimulating electrode suitable for long term chronic use.

It is another object to provide such an electrode for use in long term experimental animal studies.

Still another object is to provide such an electrode which is of relatively small size, implants firmly and does not cause adverse effects on the heart tissue.

Yet still another object is to provide such an electrode for use on infarcted laboratory animals in conscious animal experimental studies.

Upon further study of the specification and appended claims, further objects and advantages of this invention will become apparent to those skilled in the art.

In accordance with one aspect of the invention, the bipolar electrode is constructed as a bio-compatible non-conductive material structure, such as, a silicone rubber disc. First and second conducting wires are embedded in the silicone rubber disc with electrode bead shaped means attached at the end of each wire and projecting outwardly, both from the same side of the disc, to constitute the conductive electrode contacts of the electrode. In a preferred aspect, the beads are made of solid silver.

In a more preferred aspect, the invention will be a disc made of polypropylene mesh, typically mono-filament open mesh of 105 micron. The disc will have been cut from such a mesh to a size of about a 0.8 cm disc with the edges having been heat sealed in a conventional manner to prevent fraying. In this case two lengths of silver plated multi-strand conductive wire, commercially available under the designation Cat. No. AS155-28 from Cooner Wire Company in Chatsworth, Calif., are threaded through the disc, the wire being covered with insulation, and oriented at the ends, on the same side of the disc, about 0.5 cm apart +/−0.1 cm. The stripped ends of the wires are tied into secure knots and the excess trimmed off. The wires are further secured with silk suture, of appropriate size, to the disc with any exposed bare wire not making up the contact being sealed and insulated with medical grade silicon adhesive.

Although a specific type of wire has been designated for use in practicing the invention, it will be readily apparent that any brand of 28 gauge multi-strand silver-plated wire will work provided it is insulated with silicone rubber. With respect to the mesh discs, these are cut to size from polypropylene or nylon monofilament mesh sheets commercially available from Small Parts Inc., Miami, Fla. The silicone discs are cut to size from Silastic brand sheeting, commercially available through Dow Corning Corp., Medical Products Division, Midland, Mich. Although specific sources have been designated for the disc material, it too is to be noted that these are conventional materials well known to those of ordinary skill in the art, and readily available to enable the practice of the invention.

In both embodiments the disc is attached to the heart of an experimental animal, for example, the right ventricle, of an infarcted dog for conducting testing. In the case of the mesh discs advantages are obtained by the fact that the mesh structure permits growth of tissue into the mesh for more secure attachment. At the same time, the small size of the conducting portions, i.e., the beads or wire knots, ensures little damage caused by current with a consequent reduction in resulting scar tissue. The use of silver ensures sufficient current carrying capacity.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION OF THE INVENTION

Figure 1:
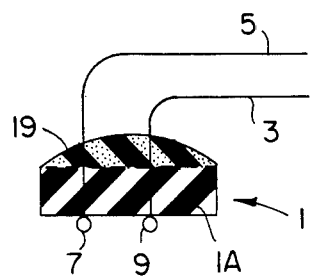
FIG. 1 is a side cross-sectional view of a first embodiment of the bipolar electrode of the invention.
Figure 2:
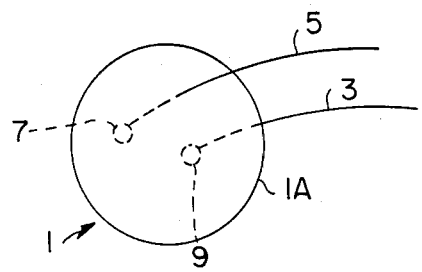
FIG. 2 is a bottom view of the electrode of FIG. 1.

In FIGS. 1 and 2, there is shown a first embodiment of the bipolar electrode 1 of the invention. The electrode 1 is a silicone disc 1A having two wires 3 and 5 passing through the discs 1A from one side with the ends thereof extending outwardly, out the other side of disc 1A. In this case the disc 1A will be of about 8 mm diameter and 1.5 mm in thickness, with the ends of the wires spaced about 0.5 cm apart +/−0.1 cm. At the ends of the wires 3 and 5 are solid silver spheres of typically 1.0 mm diameter soldered thereto and projecting from the disc.

The wires 3 and 5 of the electrode 1 are typically multi-strand silver plated copper wire insulated with silicone rubber, and are of about 0.33 mm in diameter and 60 cm in length. The disc 1A is made of medical grade silicon and the wires sealed to the disc at the top surface by medical grade silicone adhesive 19.

This embodiment is particularly advantageous for use in chronic attachment situations with little or no adverse effects. The durability of the electrode is high when compared to those presently on the market. The use of a silicone disc body offers unlimited attachment sites for suture application to tissue surfaces. This aspect is particularly invaluable when "on site" orientation changes must be made because of anatomical anomalies preventing standard orientation.

Figure 3:
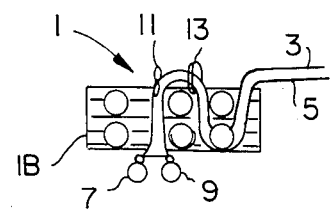
FIG. 3 is a cross-sectional side view of an alternative, and more preferred, embodiment of the electrode of the invention, showing the mesh structure thereof.
Figure 4:
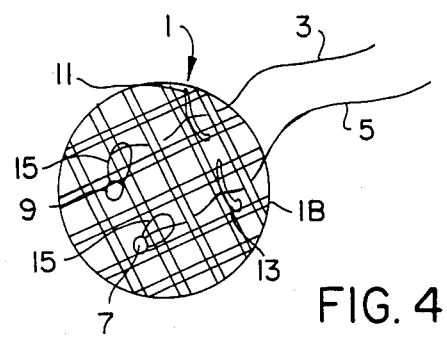
FIG. 4 is a bottom view of the electrode of FIG. 3.

In the embodiment of the electrode illustrated in FIGS. 3 and 4, the electrode 1 is made up of a mesh disc 1B. The disc 1B is a mesh disc of polypropylene mesh, mono-filament open mesh of 105 micron, cut from a large mesh into a disc of about 0.8–1.5 cm. The edges of the disc 1B are heat sealed to prevent fraying.

Two lengths of multi-stranded silver plated wire 3 and 5, as above, which are from one source, as described above, commercially available under the designation (#AS155-28), are threaded through the disc 1B, as is more clearly shown in FIG. 4. The ends project out one side of the disc 1B and are stripped and tied into knots to serve as the electrode conductive contacts 7 and 9. The remaining portions of the wires 3 and 5 are insulated with silicone rubber. The wires 3 and 5 are attached to the mesh 17 of disc 1B by means of sutures 11 of silk thread. The stripped portions of the wires not tied are covered with medical grade silicone adhesive 15.

This embodiment shows improved performance over that of FIGS. 1 and 2 by solving the problem of occasional detachment. More particularly, the mesh structure permits ingrowth of fibrous tissue into the mesh enhancing attachment at the site.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The following examples involve study of mongrel dogs, more than three days following the surgery which implanted the electrodes and produced the myocardial infarct. In the tests the stimulating electrodes are used in an ongoing screening model to test the efficacy of standard and novel antiarrhythmic agents.

EXAMPLE 1

Two electrodes of the polypropylene mesh type as disclosed are sutured to the surface of a dog's heart at the time of implantation surgery. One electrode is positioned at the base of the right ventricle. Another electrode is positioned on the left atrium. The adjoining wires of the electrodes are exteriorized subdermally to the back of the neck where they are secured in an electricl connector and wrapped in a collar until time of use.

The dog is brought into the lab for study and placed individually in a large acrylic cage to allow for freedom of movement. The dog is fitted with a jacket which holds a blood pressure transducer and electrical connectors for the stimulating electrodes. After an equilibration period, the atrium and ventricle are stimulated using bipolar, square wave stimuli; 2 milliseconds in duration at a basic cycle length sufficient to override intrinsic heart rate.

Experimental ventricular arrythmias are initiated using either a synchronous or random train stimulation protocol. The synchronous stimulation protocol involves the initiation of experimental ventricular arrhythmias using $1(S_2)$ or $2(S_3)$ extra stimuli. The random train protocol involves using a train of extra stimuli; either 3 or 5 beats in length at cycle lengths of 120–200 milliseconds.

After months of initial implantation and testing being concluded, investigations show that the electrodes are securely attached due in part to tissue ingrowth into the mesh and suture attachment. Little or no scarring due to electrical stimulation is observed.

EXAMPLE 2

Two electrodes of the silicone disc type as discussed are sutured to the surface of a dog's heart substantially as discussed in Example 1 in the case the mesh type electrode. This is done on several different dogs. Investigations conducted after several months reveal that a few of the electrodes are detached. Substantially no scarring due to electrode contact is observed.

EXAMPLE 3

Commercially available bipolar electrodes are attached as in Examples 1 and 2. The testing is substantially the same as above. The electrodes are polyvinyl plaques with silver electrodes and three feet of wire. Over chronic use a high incidence of polyvinyl tearing and wire breakage due to repeated flexing is observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A bipolar electrode member specifically for attachment to a heart by suturing, the electrode comprising:
    a disc of bio-compatible, electrically insulating material, the disc having first and second opposed surfaces, a selected thickness and an edge surface joining the first and second surfaces;
    a pair of spaced bores extending through the disc from the first surface to the second surface;
    a wire extending through each bore, each wire terminating in a bead disposed on the second surface of the disc and projecting therefrom to form a pair of spaced electrodes, and
    means on the first surface for securing the wires to the disc.

2. The bipolar electrode of claim 1 wherein the disc is made of silicone rubber and wherein the means for securing the wires to the disc is silicone adhesive.

3. The bipolar electrode of claim 2 wherein the beads are pure silver, are spherical in configuration and are soldered to the wires and wherein the wires are multi-strand, silver plated copper wires.

4. The bipolar electrode of claim 3 wherein the beads are approximately 1.0 mm in diameter and are spaced about 0.4–0.6 cm apart with the disc having a diameter of 8 mm and a thickness of 1.5 mm; the wires being insulated with silicon rubber and having a diameter of approximately 0.33 mm.

5. The bipolar electrode of claim 1 wherein the disc is made of polypropylene mesh, the edge surface thereof being fired by heat, wherein tissue can grow through the mesh; the beads being formed of knots tied in the free ends of the wire.

6. The bipolar electrode of claim 5 wherein the wires are secured to the disc by sutures.

7. The bipolar electrode of claim 6 wherein the polypropylene is a mono-filament open mesh of about 105 micron.

8. The bipolar electrode of claim 7 wherein the wires are silver plated copper wires having a diameter of approximately 0.33 mm.

* * * * *